United States Patent [19]
Kojima et al.

[11] Patent Number: 5,132,997
[45] Date of Patent: Jul. 21, 1992

[54] X-RAY SPECTROSCOPIC ANALYZING APPARATUS

[75] Inventors: Shinjiro Kojima; Tadashi Utaka, both of Takatsuki, Japan

[73] Assignee: Rigaku Industrial Corporation, Osaka, Japan

[21] Appl. No.: 754,908

[22] Filed: Sep. 4, 1991

[30] Foreign Application Priority Data

Sep. 5, 1990 [JP] Japan .................. 2-236127

[51] Int. Cl.$^5$ .............................. G21K 1/06
[52] U.S. Cl. ........................ 378/85; 378/49; 378/83
[58] Field of Search .................. 378/49, 82–85

[56] References Cited
U.S. PATENT DOCUMENTS 4,884,290 11/1989 Tamura et al. ................. 378/85

Primary Examiner—Craig E. Church
Attorney, Agent, or Firm—Graybeal Jackson Haley & Johnson

[57] ABSTRACT

An X-ray spectroscopic analyzing apparatus which comprises a source of X-rays, a first analyzing crystal for diffracting the X-rays from the X-ray source, and a second analyzing crystal for diffracting the X-rays from the X-ray source and also for passing therethrough a diffracted X-ray component from the first analyzing crystal. The first and second analyzing crystals are so disposed and so positioned as to permit the diffracted X-ray components of different wavelengths to travel along a single path towards a sample to be analyzed. On an optical path extending between the X-ray source and the sample, a filtering means for cutting a portion of the X-rays which has a wavelength shorter than a predetermined wavelength.

9 Claims, 7 Drawing Sheets

X-RAY SPECTROSCOPIC ANALYZING APPARATUS

BACKGROUND OF THE INVENTION

1. Field of the Invention

The present invention relates to an X-ray spectroscopic analyzing apparatus having a source of X-rays for radiation onto a sample to be analyzed.

2. Description of the Prior Art

As an apparatus for achieving an elemental analysis of a sample to be analyzed, a fluorescent X-ray analyzing apparatus has been known which comprises a source of X-rays, for example, an X-ray tube, for radiating an excitation X-ray beam towards a sample to be analyzed, and a fluorescent X-ray detector for detecting the intensity of fluorescent X-rays coming from the sample to determine elements contained in the sample, In this type of fluorescent X-ray analyzing apparatus, a low-order beam having a relatively high intensity is spectroscopically selected from a spectrum of the X-rays emitted from the X-ray tube and is used as the excitation X-rays.

With the prior art fluorescent X-ray analyzing apparatus, it has been found that no element of the sample having a wavelength component lower than that of the low-order beam cannot be spectroscopically determined. Accordingly, where the sample contains the same element as that contained in a target material of the X-ray tube, the spectroscopic determination of such element is not possible.

By way of example, if the target material is made of tungsten (W), and so long as a $WL\beta_1$ beam ($\lambda = 1.2818$ Å, $E = 9.671$ keV) having a relatively high intensity is employed for the excitation X-ray beam, the determination of the presence of tungsten in the sample is not possible even though the sample in fact contain tungsten. This is because the wavelength at the absorption edge peculiar to tungsten is shorter than the wavelength of the $WL\beta_1$ beam.

This is also true of other elements than tungsten. By way of example, arsenic cannot be spectroscopically analyzed with the prior art fluorescent X-ray analyzing apparatus because the wavelength ($\lambda = 1.045$ Å) at the absorption edge peculiar to arsenic is shorter than the wavelength of the $WL\beta_1$ beam.

Apart from the foregoing prior art, a total reflection fluorescent X-ray analyzing method is also well known in which a primary X-ray beam is radiated so as to be incident upon a sample to be analyzed at a minute angle of incidence so that fluorescent X-rays reflected from a surface region of the sample can be analyzed for the elemental determination. In the practice of this prior art fluorescent X-ray spectroscopic analyzing method utilizing the total reflection, a monochromatic light is employed for the primary X-ray beam. However, where the monochromatic light is employed, it has often been observed that the spectroscopic analysis tends to result in a measurement error depending on preset values of parameters used during the analysis.

SUMMARY OF THE INVENTION

Accordingly, the present invention has for its important object to provide an improved X-ray spectroscopic analyzing apparatus effectively utilizable for the analysis of an element having a wavelength at the absorption edge which is shorter than that of the low-order beam of relatively high intensity contained in the spectrum of the excitation X-rays.

Another important object of the present invention is to provide an improved X-ray spectroscopic analyzing apparatus of the type referred to above, which can be effectively utilized in the practice of the fluorescent X-ray analyzing method using the total reflection with a minimized measurement error, thereby to improve the reliability of the elemental determination.

In order to accomplish the foregoing objects, in accordance with the present invention, there is provided a X-ray spectroscopic analyzing apparatus which comprises a source of X-rays, a first analyzing crystal for diffracting the X-rays from the X-ray source, and a second analyzing crystal for diffracting the X-rays from the X-ray source and also for passing therethrough a diffracted X-ray component from the first analyzing crystal. The first and second analyzing crystals are so disposed and so positioned as to permit the diffracted X-ray components of different wavelengths to travel along a single path towards a sample to be analyzed. On an optical path extending between the X-ray source and the sample, a filtering means for cutting a portion of the X-rays which has a wavelength shorter than a predetermined wavelength.

Preferably, the X-ray spectroscopic analyzing apparatus of the above described construction may be provided with a shutter means for selectively causing one of the diffracted X-ray components to be incident upon the sample to be analyzed.

According to one aspect of the present invention, since the use has been made of the two analyzing crystals, one of the two analyzing crystals may be used to diffract a low-order beam of X-ray having a relatively high intensity and the other of the two analyzing crystals may be used to diffract a continuous X-ray beam having a predetermined wavelength or a high-order beam of X-ray having a relatively low intensity. Therefore, an excitation X-ray beam comprised of the low-order beam and an X-ray beam component having a wavelength shorter than that of the low-order beam can be obtained.

Also, according to another aspect of the present invention, the use of the two X-ray beam components used for the elemental analysis as discussed above makes it possible to average measurement errors attributable to preset values of various parameters and, therefore, any possible measurement error can be minimized advantageously.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings, like reference numerals are used to denote like parts throughout the several views, and:

DETAILED DESCRIPTION OF THE EMBODIMENTS

Figure 1:
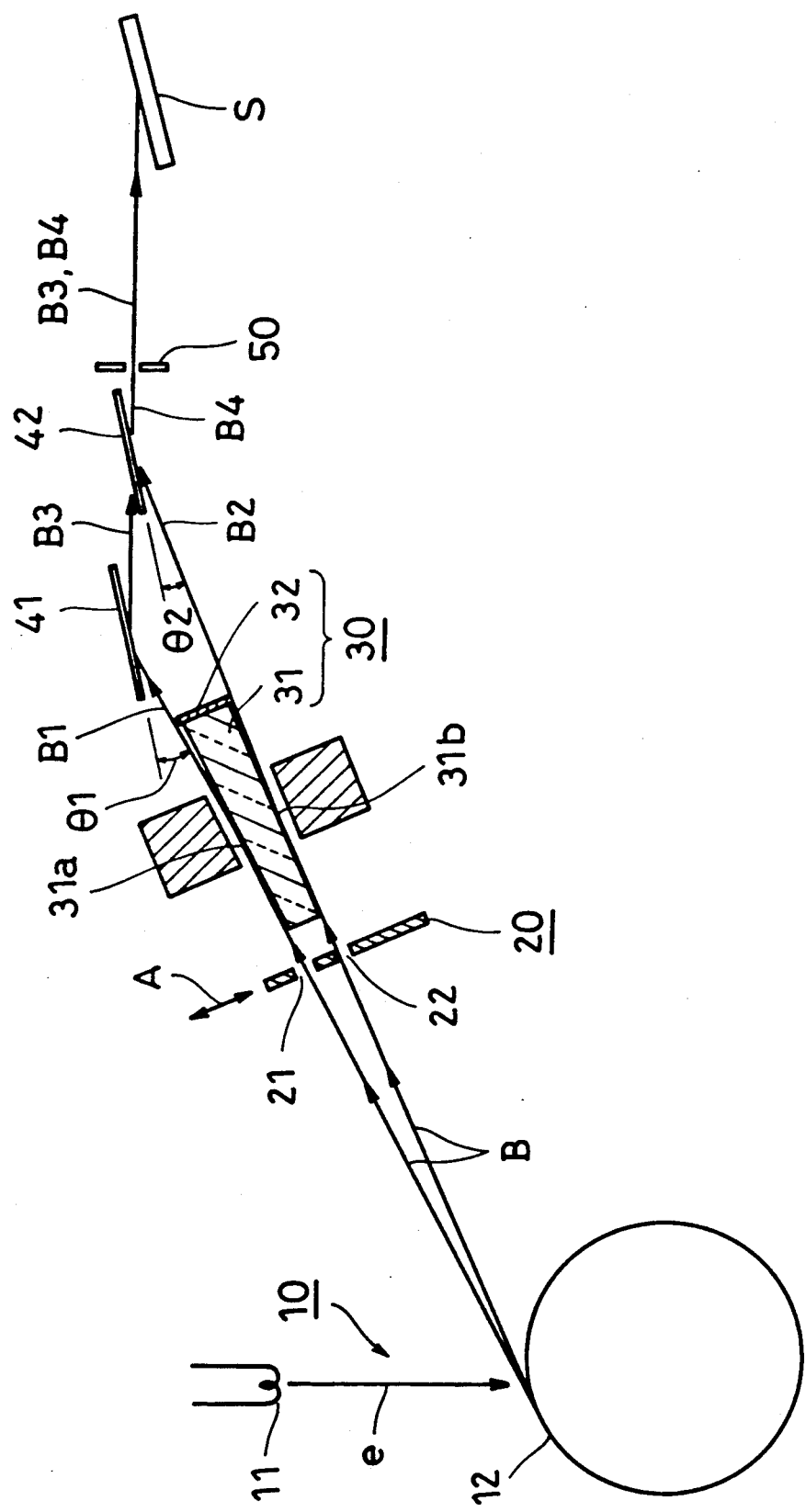
FIG. 1 is a schematic diagram showing an X-ray spectroscopic analyzing apparatus according to a first prefered embodiment of the present invention.
Figure 2:
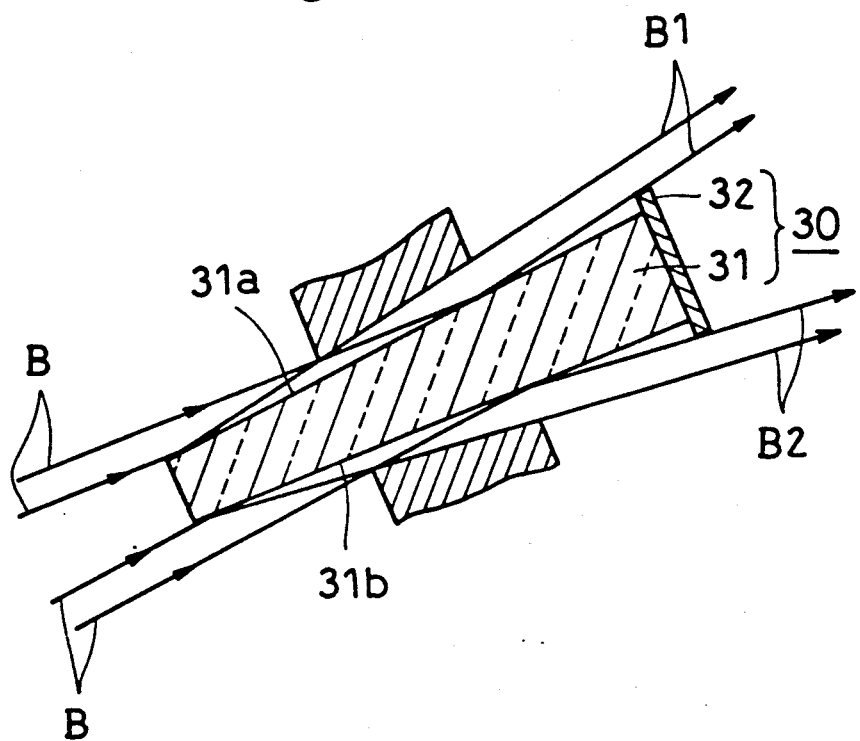
FIG. 2 is a schematic sectional view, on an enlarged scale, showing a filtering means used in the X-ray spectroscopic analyzing apparatus shown in FIG. 1.
Figure 3:
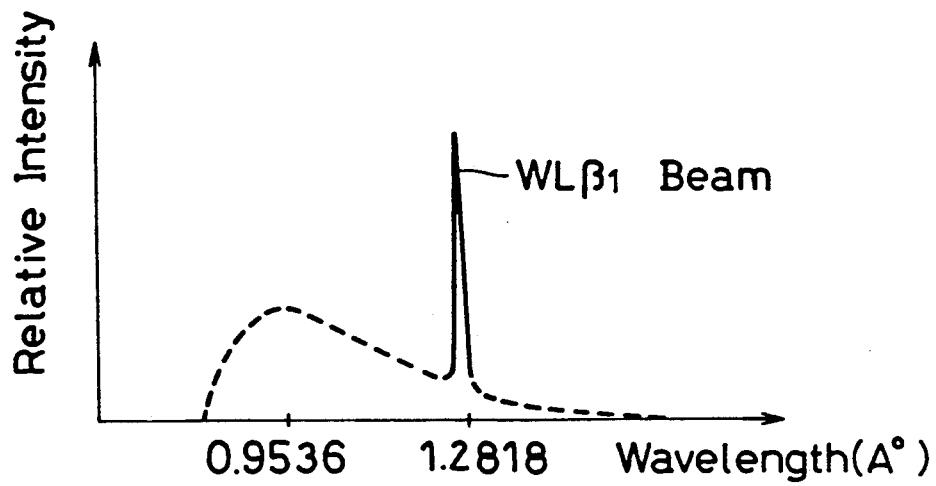
FIG. 3 is a graph showing a spectrum of fluorescent X-rays.

With reference to FIGS. 1 to 3, an X-ray spectroscopic analyzing apparatus according to a first preferred embodiment of the present invention will be described.

Referring first to FIG. 1, the apparatus shown therein comprises a source of X-rays, for example, an X-ray tube 10 having a filament 11 from which electrons e are radiated so as to impinge upon a rotary target 12 which comprises a rotary drum having its outer peripheral surface coated or deposited with a target material. Consequent upon the impingement of the electrons e upon the rotary target 12, an X-ray beam B having an X-ray spectrum peculiar to the target material as shown in FIG. 3 is emitted from the target material forming the rotary target 12.

The X-ray beam B emitted from the target material as described above travels towards a shutter means 20 which is, so far used in the illustrated embodiment, supported for movement in a direction generally perpendicular to the path of travel of the X-ray beam B, as shown by the arrow A, and capable of assuming one of intercepting and open positions. The shutter means 20 has a pair of parallel slits 21 and 22 defined therein. This shutter means 20 is operable to intercept completely the passage of the X-ray beam B there-through when in the intercepting position, but to intercept a portion of the X-ray beam B while dividing the remaining portion of the X-ray beam B into two beam components when in the open position.

The X-ray beam components B having passed through the slits 21 and 22, respectively, travel towards a total reflection mirror 31 so as to be incident upon first and second reflecting surfaces 31a and 31b of a total reflection mirror 31 at a minute angle of incidence. The total reflection mirror 31 is employed in the form of a prism of a generally trapezoidal shape having the first and second reflecting surfaces 31a and 31b which are substantially opposite to each other, but lie in respective planes inclined so as to converge towards the rotary target 12 and, hence, in a direction confronting the direction in which the X-ray beam components B travel towards the total reflection mirror 31.

The total reflection mirror 31 is so designed and so positioned as to have the first and second reflecting surfaces 31a and 31b reflect portions of a spectrum of the X-ray beam B which have respective wavelengths longer than a predetermined wavelength. Those portions of the spectrum of the X-ray beam B reflected by the respective first and second reflecting surfaces 31a and 31b of the total reflection mirror 31 are hereinafter referred to as first and second reflected X-ray components B1 and B2, respectively. On the other hand, of the spectrum of the X-ray beam B coming from the rotary target 12, a beam portion having a wavelength shorter than the predetermined wavelength passes through the total reflection mirror 31 and is subsequently intercepted by a beam stopper 32 which is formed on, or otherwise fitted to, a surface of the total reflection mirror 31 which corresponds in position to the base of the trapezoidal shape of the total reflection mirror or prism 31.

It is to be noted that the total reflection mirror 31 and the beam stopper 32 altogether form a filtering means 30 forming an important feature of the present invention. So far illustrated in connection with the embodiment of FIGS. 1 to 3, the filtering means 30 including the total reflection mirror 31 and the beam stopper 32 is disposed on that portion of the optical path extending from the X-ray tube 10 to a sample S to be analyzed, which lies between the X-ray tube 10 and a set of first and second analyzing crystals 41 and 42 as will be described later.

The first and second reflected X-ray components B1 and B2 reflected from the first and second reflecting surfaces 31a and 31b of the total reflection mirror 31 subsequently impinge upon the first and second analyzing crystals 41 and 42 at angles $\theta1$ and $\theta2$ of incidence, respectively. Each of the first and second analyzing crystals 41 and 42 is operable to diffract the associated first or second reflected X-ray component B1 or B2 to provide a first or second diffracted X-ray component B3 or B4 of a wavelength satisfying the following Bragg's formula:

$$2d \cdot \sin \theta = n\lambda$$

wherein d represents an interplanar distance of the crystal; $\theta$ represents the angle of incidence; $\lambda$ represents the wavelength of the diffracted X-ray component; and n represents the power of reflection expressed by an integer (i.e., 1, 2, 3, ...).

In the practice of the present invention, the angle of incidence of the X-ray beam B upon the reflecting surface 31a of the total reflection mirror 31 is chosen to be so small that both of a portion of continuous X-ray beam having a wavelength shorter than the first-order X-ray beam and the X-ray beam having a wavelength longer than the wavelength thereof can be reflected by the surface 31a of the total reflection mirror 31. Similarly, the angle of incidence of the X-ray beam B upon the reflecting surface 31b of the total reflection mirror 31 is chosen to be so large that both of the first-order X-ray beam having a relatively long wavelength and a X-ray beam having a wavelength longer than the wavelength thereof can be reflected by the surface 31b of the total reflection mirror 31.

Also, the angle $\theta_1$ of incidence of the X-ray component B1 upon the first analyzing crystal 41 is so chosen to be of a value effective to diffract a portion of the continuous X-ray including high-order beams to satisfy the Bragg's formula, and similarly, the angle $\theta_2$ of incidence of the X-ray component B2 upon the second analyzing crystal 42 is so chosen to be of a value effective to diffract the first-order X-ray to satisfy the Bragg's formula.

The second analyzing crystal 42 is disposed on a path of travel of the first diffracted X-ray component B3, while the first and second analyzing crystals 41 and 42 are so disposed and so positioned that the first and second diffracted X-ray components B3 and B4 reflected respectively from the first and second analyzing crystals 41 and 42 can travel along the same path towards the sample S to be analyzed. Accordingly, the first diffracted X-ray component B3 can, after having passed through the second analyzing crystal 42, travel towards and subsequently impinges upon the sample S to be analyzed, having passed along the same path as that along which the second diffracted X-ray component B4 reflected from the second analyzing crystal 42 travels and subsequently impinges upon the same sample S to be analyzed.

Disposed on the path between the second analyzing crystal 42 and the sample S to be analyzed is an exit slit 50 through which both of the first and second diffracted X-ray components B3 and B4 pass before they reach the sample S to be analyzed.

A specific example of the spectroscopic measurement using the apparatus of the present invention will now be described.

Assuming that the target material for the rotary target 12 is chosen to be tungsten, the X-ray beam is comprised of the low-order beam such as the $WL\beta_1$ beam (the first-order X-ray) shown by the solid line in FIG. 3, and the continuous X-ray shown by the broken line in FIG. 3. The reflecting surface 31a of the total reflection mirror 31 shown in FIGS. 1 and 2 serves to cut the X-ray beam B which is a portion of the continuous X-ray having an energy (i.e., a wavelength) greater than 13 keV ($\lambda = 0.9536$ Å), while the reflecting surface 31b of the total reflection mirror 31 serves to cut the X-ray beam B having an energy (i.e., a wavelength) greater than that of the $WL\beta_1$ beam ($\lambda = 1.2828$ Å) which is the first-order X-ray.

In this example, the first analyzing crystal 41 is made of a fluorinated lithium (LiF. 2d = 4.0273 Å, (200) plane serving as a reflecting surface) with the spectral angle $2\theta$ set at 27.387°), and second analyzing crystal 42 is made of graphite (2d = 6.708 Å, (0002) plane serving as a reflecting surface) with the spectral angle $2\theta$ set at 22.032°. Hence, according to the Bragg's formula referred to hereinbefore, the first analyzing crystal 41 is effective to reflect the diffracted X-ray component ($\lambda = 0.9536$ Å) of 13 keV in energy when the first reflected X-ray component B1 is incident upon the first analyzing crystal 41 and, on the other hand, the second analyzing crystal 42 is effective to reflect the $WL\beta_1$ beam ($\lambda = 1.2828$ Å) when the second reflected X-ray component B2 is incident upon the second analyzing crystal 42.

Accordingly, even though the target material for the rotary target 12 is tungsten, the first diffracted X-ray component B3 of 13 keV which is greater than the energy of the $WL\beta_1$ beam can be used as the excitation X-rays for radiation onto the sample S to be analyzed and, therefore, even though the sample S to be analyzed contains such elements as tungsten and arsenic having a wavelength at the absorption edge which is shorter than the wavelength of the $WL\beta_1$ beam, the determination of the presence of such elements in the sample S is possible.

Where other elements each having a wavelength at the absorption edge which is longer than the wavelength of the $WL\beta_1$ beam are desired to be analyzed, the second diffracted X-ray component B4 comprised of the $WL\beta_1$ beam having a relatively high density can be effectively utilized as the excitation X-rays.

Instead of the use of tungsten for the target material, Au may also be employed therefor. In such case, the first and second diffracted X-ray components B3 and B4 may be an AuL$\gamma$ beam ($\lambda = 0.9205$ Å, E = 13.38 keV) and an AuL$\alpha$ beam ($\lambda = 1.2764$ Å, E = 9.73 keV), respectively.

Also, in the practice of the present invention, a fluorinated lithium (LiF. 2d = 2.848 Å, (220) plane serving as a reflecting surface), and a fluorinated lithium (LiF. 2d = 4.0273 Å, (200) plane serving as a reflecting surface) may be employed as alternative material for the first and second analyzing crystals 41 and 42, respectively.

Figure 4:
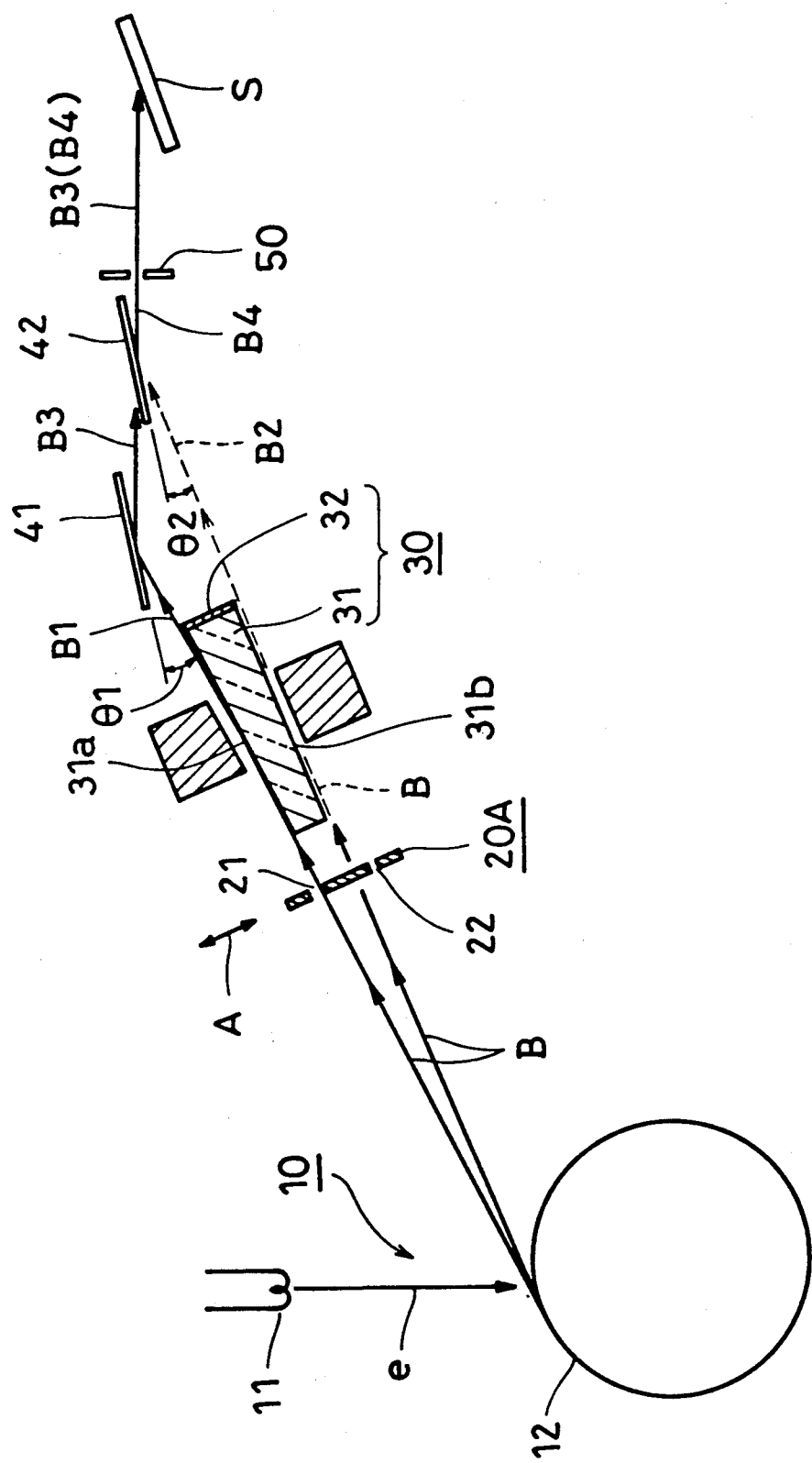
FIG. 4 is the schematic diagram showing an X-ray spectroscopic analyzing apparatus according to a second preferred embodiment of the present invention.

Referring now to FIG. 4, a second preferred embodiment of the present invention will be described. According to this embodiment of the present invention, a shutter means 20A corresponding in function to the shutter means 20 used in the foregoing embodiment is so designed and so positioned that the slits 21 and 22 can be alternately brought into alignment with the path of travel of the X-ray beam B. In other words, the slits 21 and 22 of the shutter means 20A are alternately closed and opened, respectively. Thus, it will readily be understood that the first and second diffracted X-ray components B3 and B4 are alternately impinged upon the sample S to be analyzed.

Except for the difference lying in the design of the shutter means, the apparatus according to the second preferred embodiment of the present invention is similar to and function in a manner substantially similar to that according to the foregoing embodiment and, therefore, the details thereof will not be reiterated for the sake of brevity.

The X-ray spectroscopic analyzing apparatus constructed according to the second preferred embodiment of the present invention can be advantageously employed in the practice of a total reflection fluorescent X-ray analysis which will now be described with reference to FIGS. 5 to 12.

Figure 5:
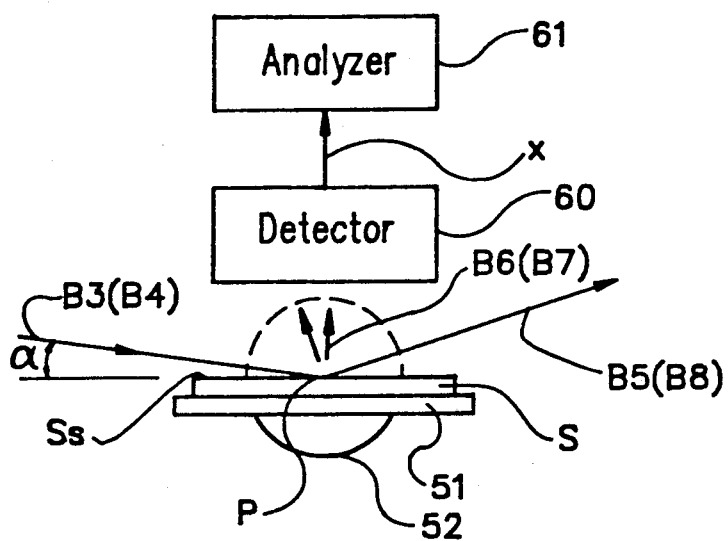
FIG. 5 is a schematic diagram showing a total reflection fluorescent X-ray analyzing system utilizing the X-ray spectroscopic analyzing apparatus according to the present invention.
Figure 6:
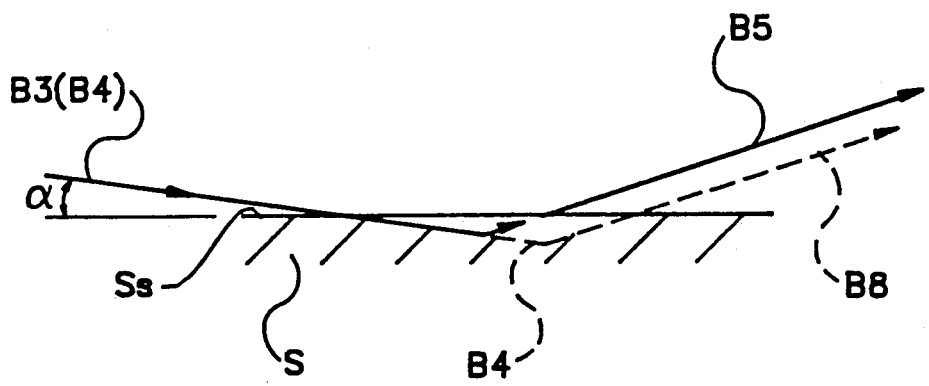
FIG. 6 is a diagram showing, on an exaggerated scale, a path of travel of X-rays towards a sample to be analyzed.
Figure 7A:
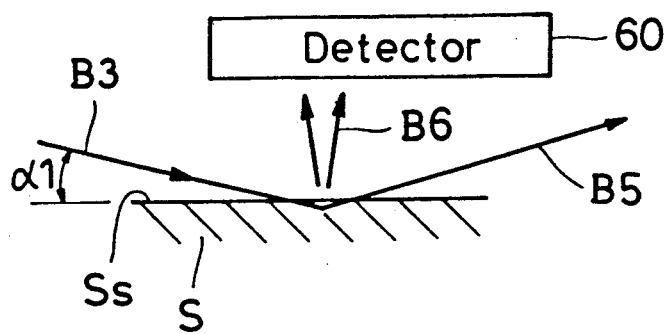
FIG. 7 comprised of FIGS. 7(a) to 7(d) illustrates the sequence of measurement carried out by the use of the X-ray spectroscopic analyzing apparatus according to the present invention.
Figure 7B:
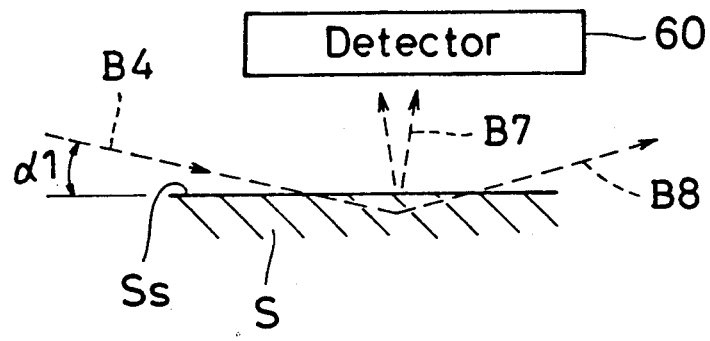
Figure 7C:
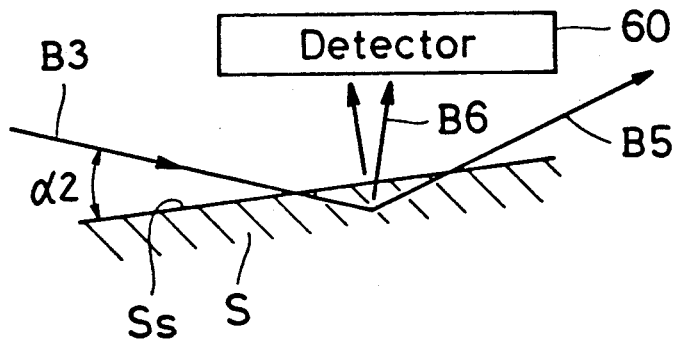
Figure 7D:
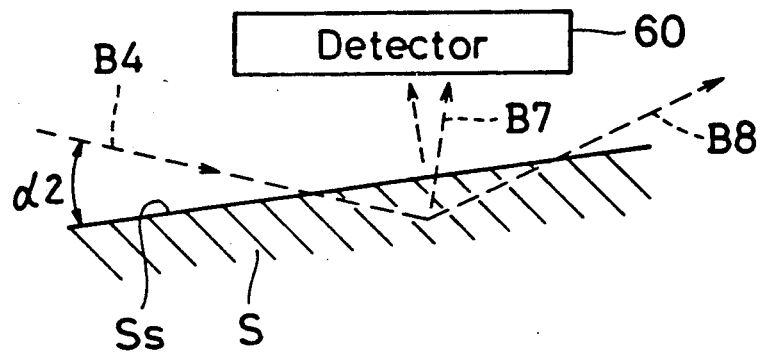

Referring first to FIG. 5, the sample S to be analyzed is employed in the form of a semiconductor wafer made of silicon and containing impurities such as arsenic injected thereinto. The sample S has a sample surface Ss adapted to be radiated by the first and second diffracted X-ray components B3 and B4 having travelled along the single and same path. Each of the first and second diffracted X-ray components B3 and B4 is in the form of a monochromatic beam of light having a wavelength shorter than the absorption edge wavelength of an element to be determined, for example, arsenic, which is contained in the sample S. By way of example, tungsten may be employed for the target material of the rotary target 12, and the second diffracted X-ray component B4 may be chosen the WL$\beta_1$ beam of a kind having a wavelength $\lambda 2$ somewhat shorter than the absorption edge wavelength thereof while the first diffracted X-ray component B3 may be chosen the 13 keV beam having a wavelength $\lambda 1$ shorter than the wavelength $\lambda 2$, for example, ⅛ to ¼ of the absorption edge wavelength thereof.

So far shown in FIG. 5, the sample S to be analyzed is placed on a sample bench 51 adapted to be driven by a drive unit 52 so as to tilt through a minute angle about the point P of incidence of the diffracted X-ray components B3 and B4 on the sample surface Ss of the sample S to be analyzed. While the angle of incidence identified by $\alpha$ defined between the sample surface Ss and the direction of incidence of the diffracted X-ray components B3 and B4 is adjustable with a tilting motion of the sample bench 51, the angle $\alpha$ of incidence is selected to be within the range of 0.01 to 0.2 degree so that the total reflection can take place from the sample surface Ss of the sample S to be analyzed.

The determination of the element contained in the sample S is carried out in the following manner.

At the outset, only the first slit 21 of the shutter means 20A shown in FIG. 4 is brought into alignment with the path of travel of the X-ray beam B reflected from the rotary target 12 so that, as shown in FIG. 7($a$), the first diffracted X-ray component B3 can impinge upon the sample surface Ss at a specific angle $\alpha 1$ of incidence. Then, a portion of the first diffracted X-ray component B3 which has been impinged upon the sample surface Ss undergoes the total reflection therefrom thereby to provide a reflected X-ray component B5, while the remaining portion of the first diffracted X-ray component B3 impinging upon the sample surface Ss excites an element present in a surface region (of a depth ranging from 10 to 20 Å) of the sample surface Ss. When the element in the surface region of the sample surface Ss is so excited, the element emits a first fluorescent X-ray component B6 of a wavelength peculiar to such element.

The first fluorescent X-ray component B6 emitted from the element in the sample S travels towards a fluorescent X-ray detector 60 by which the intensity I of the X-ray component can be detected.

Thereafter, only the second slit 22 of the shutter means 20A is brought into alignment with the path of travel of the X-ray beam B reflected from the rotary target 12 so that, as shown in FIG. 7($b$), the second diffracted X-ray component B4 can impinge upon the sample surface Ss at the same angle $\alpha 1$ of incidence. Then, in a manner similar to the first diffracted X-ray component B3 described hereinabove, a portion of the second diffracted X-ray component B4 which has been impinged upon the sample surface Ss undergoes the total reflection therefrom thereby to provide a reflected X-ray component B8, while the remaining portion of the second diffracted X-ray component B4 impinging upon the sample surface Ss excites an element present in the surface region of the sample surface Ss. When the element in the surface region of the sample surface Ss is so excited, the element emits a second fluorescent X-ray component B7 of a wavelength peculiar to such element.

Thus, the second fluorescent X-ray component B7 emitted from the sample S is subsequently detected by the fluorescent X-ray detector 60 to determine the intensity I of the X-ray component.

Thereafter, the sample S is somewhat tilted by driving the sample bench 51 shown in FIG. 5 so that the angle $\alpha 2$ of incidence can have a value greater than the angle $\alpha 1$ of incidence shown in FIG. 7($a$). With the sample surface Ss held at the angle $\alpha 2$ of incidence, procedures similar to those shown in and described with reference to FIGS. 7($a$) and 7($b$) are repeated.

Specifically, the sample surface Ss is again radiated by the first diffracted X-ray component B3 in a manner similar to that described with reference to FIG. 7($a$). However, since the angle $\alpha 2$ of incidence is greater than the angle $\alpha 1$ of incidence, the first diffracted X-ray component B3 penetrates deep into the surface region of the sample S as shown in FIG. 7($c$) and, when an element present in a deeper portion of the sample S is consequently excited by such first diffracted X-ray component B3, a first fluorescent X-ray component B6 is subsequently emitted from such deeper portion of the sample S. The first fluorescent X-ray component B6 is subsequently detected by the fluorescent X-ray detector 60 to determine the intensity I of the X-ray component.

Similarly, the second diffracted X-ray component B4 is impinged upon the sample surface Ss, as shown in FIG. 7($d$), in a manner similar to that described with reference to FIG. 7($b$). By a similar reason as described with reference to FIG. 7($b$), that portion of the second diffracted X-ray component B4 which has been impinged upon the sample surface Ss undergoes the total reflection therefrom thereby to provide a reflected X-ray component B8, while the remaining portion of the second diffracted X-ray component B4 impinging upon the sample surface Ss excites an element present in the surface region of the sample surface Ss. When the element in the surface region of the sample surface Ss is so excited, as shown in FIG. 7($d$), the element emits a second fluorescent X-ray component B7 of a wavelength peculiar to such element which is subsequently detected by the fluorescent X-ray detector 60 to determine the intensity I of the X-ray component.

Figure 8:
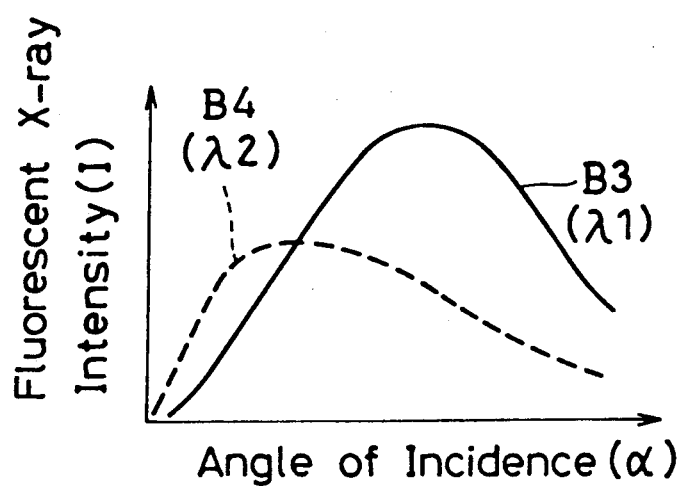
FIG. 8 is a characteristic graph showing a result of measurement of the intensity of the fluorescent X-rays relative to the angle $\alpha$ of incidence.

Thus, as hereinbefore described, using the different angles $\alpha$ of incidence, that is, by stepwisely varying the angle $\alpha$ of incidence, the radiation of the first and second diffracted X-ray components B3 and B4 to the sample surface Ss and the detection of the first and second fluorescent X-ray components B6 and B7 are repeated to determine the intensity I of the fluorescent X-ray component emitted from the element in the sample S at the different angle $\alpha$ of incidence of any one of the first and second diffracted X-ray components B3 and B4. As shown in FIG. 8, the intensity I of the fluorescent X-ray component varies with a change in angle $\alpha$ of incidence of the first diffracted X-ray component B3 upon the sample surface Ss as shown by the solid line, while the intensity I of the fluorescent X-ray component varies with a change in angle $\alpha$ of incidence of the second diffracted X-ray component B4, as shown by the dotted line. The fluorescent X-ray detector 60 outputs measurements descriptive of the intensity I of the fluorescent X-ray component which varies with a change in angle $\alpha$ of incidence of any one of the first and second diffracted X-ray components B3 and B4 upon the sample surface Ss.

The measurements outputted from the fluorescent X-ray detector 60 are processed by a multi-pulse height analyzer 61 in the following manner.

Figure 9:
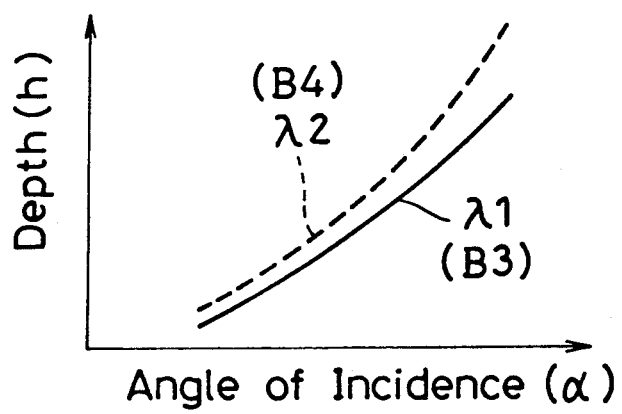
FIG. 9 is a characteristic graph showing a relationship between the angle of incidence and the depth of a surface region of the sample to be excited.
Figure 10:
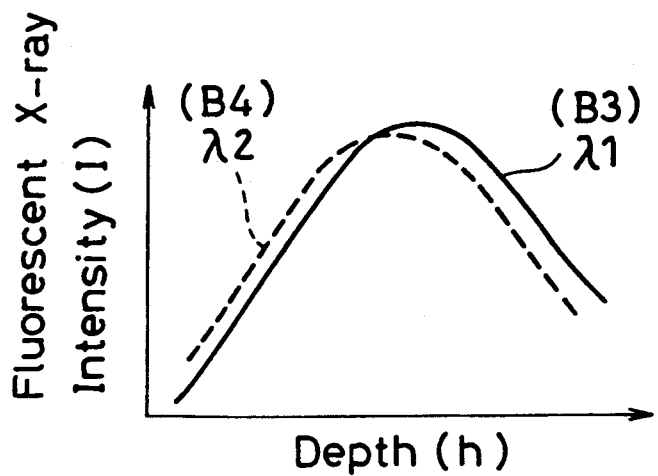
FIG. 10 is a characteristic graph showing a relationship between the depth of the surface region of the sample and the intensity of the fluorescent X-rays.

The relationship between the angle $\alpha$ of incidence of each of the first and second diffracted X-ray components B3 and B4 and the depth h of the surface region of the sample S into which the diffracted X-ray component B3 or B4 penetrates is such as shown in FIG. 9 and is generally fixed depending on the wavelength λ of the associated diffracted X-ray component B3 or B4 impinging upon the sample surface Ss. Accordingly, with this relationship determined beforehand, and from a result of detection (data outputted from the fluorescent X-ray detector 60) which is descriptive of the relationship between the angle α of incidence and the intensity I of the fluorescent X-ray components as shown in FIG. 8, the intensity I of the X-ray component emitted from a varying depth h of the sample S for each of the wavelength λ1 of the X-ray component B3 and the wavelength λ2 of the X-ray component B4 can be determined as shown in FIG. 10.

Figure 11:
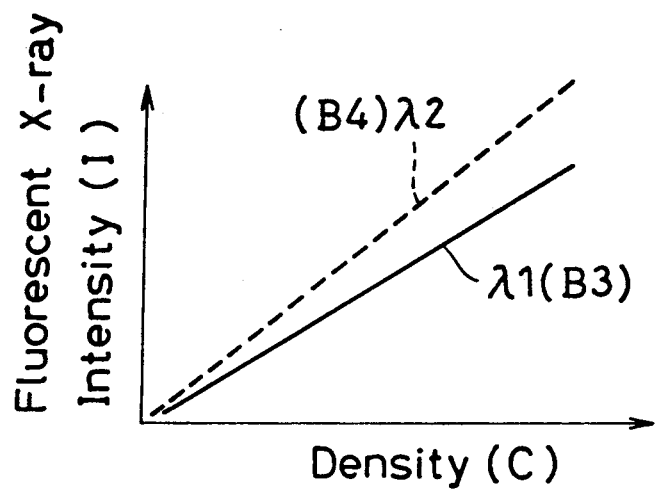
FIG. 11 is a characteristic graph showing the intensity of the fluorescent X-rays relative to the density of an element analyzed.
Figure 12:
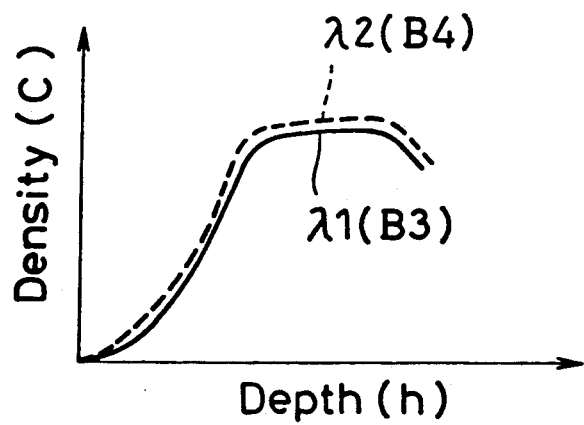
FIG. 12 is a characteristic graph showing the density of the element analyzed relative to the depth of the surface region of the sample.

The relationship between the intensity I of the fluorescent X-ray component and the density C of the element to be analyzed is fixed for each of the wavelengths λ1 and λ2 as shown in FIG. 11 and, therefore, this relationship has to be empirically determined using testpieces. From the relationship between the intensity I of the fluorescent X-ray component and the density C shown in FIG. 11 and the relationship between the depth h of the sample S and the intensity I of the fluorescent X-ray component as shown in FIG. 10, the density C of the element at the specific depth h of the sample S can be determined for each of the wavelengths λ1 and λ2.

A pattern of distribution of the densities so determined for the respective wavelengths λ1 and λ2 involves an measurement error depending on preset values of various parameters used during the analysis performed by the multi-pulse height analyzer 61 and, therefore, an averaged value of those densities is used as a distribution of the density of the element to be analyzed. In this way, even though the analysis involves the measurement error as a result of the use of the diffracted X-ray components B3 and B4 each being used in the form of the monochromatic beam of light, this measurement error can be advantageously averaged to minimize the measurement error. Hence, with the system hereinabove described according to the present invention, the reliability of the elemental analysis can be improved.

Thus, from the foregoing description of the present invention, the first and second analyzing crystals are effective to provide the excitation X-ray of a wavelength shorter than the low-order beam and the excitation X-ray comprised of a low-order beam having a relatively high density, respectively. Therefore, the spectroscopic determination of an element having an absorption edge wavelength, which is not only longer than, but also shorter than the wavelength of the low-order beam of a relatively high density, can be accomplished.

According to another aspect of the present invention, the use of the shutter mean for selectively causing one of the first and second diffracted X-ray components to be incident upon the surface of the sample to be analyzed makes it possible to allow the first and second diffracted X-ray components from the respective first and second analyzing crystals to be alternately incident upon the surface of the sample at a preselected minute angle of incidence so that the use of the total reflection fluorescent X-ray analyzing technique can result in an improved and precise spectroscopic measurement.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, although in describing any one of the foregoing embodiments of the present invention reference has been made to the use of two diffracted X-ray components B3 and B4, three or more diffracted X-ray components may be equally employed in the practice of the present invention.

Also, the filtering means 30 used in any one of the first and second preferred embodiments of the present invention has been described as positioned on the optical path between the X-ray tube 10 and the first and second analyzing crystals 41 and 42. However, in the practice of the present invention, it may be positioned at a location between the second analyzing crystal 42 and the sample S.

Accordingly, such changes and modifications are, unless they depart from the spirit and scope of the present invention as delivered from the claims annexed hereto, to be construed as included therein.

What is claimed is:
1. An X-ray spectroscopic analyzing apparatus which comprises:
   a source of X-rays;
   a first analyzing crystal for diffracting the X-rays from the X-ray source;
   a second analyzing crystal for diffracting the X-rays from the X-ray source and also for passing therethrough a diffracted X-ray component from the first analyzing crystal;
   said first and second analyzing crystals being disposed so as to permit the diffracted X-ray components of different wavelengths to travel along a single path towards a sample to be analyzed;
   a filtering means for cutting a portion of the X-rays which has a wavelength shorter than a predetermined wavelength, said filtering means being disposed on an optical path extending between the X-ray source and the sample.

2. The X-ray spectroscopic analyzing apparatus as claimed in claim 1, further comprising a shutter means for selectively causing one of the diffracted X-ray components to be incident upon the sample to be analyzed.

3. The X-ray spectroscopic analyzing apparatus as claimed in claim 1, wherein one of the first and second analyzing crystal is operable to diffract a first-order X-ray beam coming from a target material of the X-ray source, and the other of the first and second analyzing crystal is operable to diffract X-rays which have a wavelength shorter than that of the first-order beam of X-ray.

4. The X-ray spectroscopic analyzing apparatus as claimed in claim 1, wherein said filtering means is disposed on an optical path extending between the X-ray source and the first and second analyzing crystals.

5. The X-ray spectroscopic analyzing apparatus as claimed in claim 1, wherein said filtering means includes a total reflection mirror having a first and second reflecting surface for effecting a total reflection of the X-rays which have been impinged thereupon at different angles of incidence.

6. The X-ray spectroscopic analyzing apparatus as claimed in claim 2, wherein said shutter means is disposed on an optical path extending between the X-ray source and the first and second analyzing crystals.

7. The X-ray spectroscopic analyzing apparatus as claimed in claim 2, wherein said filtering means is disposed on an optical path extending between the X-ray source and the first and second analyzing crystals and said shutter means is disposed on a portion of the optical path between the X-ray source and said filtering means.

8. The X-ray spectroscopic analyzing apparatus as claimed in claim 5, wherein one of the first and second reflecting surfaces of the total reflection mirror is operable to effect a total reflection of both of a first-order X-ray beam coming from a target material of the X-ray source and an X-ray component having a wavelength longer than the wavelength of the first-order beam of X-ray, and the other of the first and second reflecting surfaces of the total reflection mirror is operable to effect a total reflection of both of an X-ray beam having a wavelength shorter than the wavelength of the first-order beam of X-ray and an X-ray component having a wavelength longer than the wavelength of said X-ray beam.

9. The X-ray spectroscopic analyzing apparatus as claimed in claim 5, wherein said filtering means comprises the total reflection mirror and a beam stopper for shielding a portion of the X-ray component which has passed through the total reflection mirror, said total reflection mirror being comprised of a prism having the first and second reflecting surfaces opposite to each other, said first and second reflecting surfaces being so inclined as to converge in a direction confronting the X-ray source, and said beam stopper being disposed on a surface of the prism which lies on one side of the prism remote from the X-ray source.

* * * * *